(12) United States Patent
Hurst et al.

(10) Patent No.: US 9,392,759 B2
(45) Date of Patent: Jul. 19, 2016

(54) NON-TRANSGENIC TOMATO VARIETIES HAVING INCREASED SHELF LIFE POST-HARVEST

(71) Applicant: Arcadia Biosciences, Inc., Davis, CA (US)

(72) Inventors: Susan R. Hurst, Seattle, WA (US); Dayna L. Loeffler, Seattle, WA (US)

(73) Assignee: Arcadia Biosciences, Inc., Davis, CA (US)

(*) Notice: Subject to any disclaimer, the term of this patent is extended or adjusted under 35 U.S.C. 154(b) by 57 days.

(21) Appl. No.: 14/325,302

(22) Filed: Jul. 7, 2014

(65) Prior Publication Data

US 2014/0317787 A1    Oct. 23, 2014

Related U.S. Application Data

(62) Division of application No. 13/123,391, filed as application No. PCT/US2009/060235 on Oct. 9, 2009, now Pat. No. 8,772,606.

(60) Provisional application No. 61/104,628, filed on Oct. 10, 2008.

(51) Int. Cl.
| | |
|---|---|
| *A01H 5/08* | (2006.01) |
| *C12N 15/01* | (2006.01) |
| *A01H 1/06* | (2006.01) |
| *C12Q 1/68* | (2006.01) |
| *C12N 15/82* | (2006.01) |

(52) U.S. Cl.
CPC .. *A01H 5/08* (2013.01); *A01H 1/06* (2013.01); *C12N 15/8261* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 5,994,075 A | 11/1999 | Goodfellow | |
| 6,180,854 B1 | 1/2001 | Morrison et al. | 800/317.4 |
| 6,762,347 B1 * | 7/2004 | Giovannoni | C07K 14/415 435/320.1 |
| 2004/0053236 A1 | 3/2004 | McCallum et al. | |
| 2005/0076410 A1 * | 4/2005 | Giovannoni | C07K 14/415 800/288 |
| 2005/0120418 A1 | 6/2005 | Fuerstenberg et al. | 800/287 |
| 2012/0054907 A1 | 3/2012 | Rose et al. | 800/278 |

OTHER PUBLICATIONS

Zhu et al. (Plant Cell Physiol. 55(1): 119-135 (2014)).*
International Search Report, International Appln. No. PCT/US2009/060235, May 24, 2010.
Written Opinion of the International Searching Authority, International Appln. No. PCT/US2009/060235, May 24, 2010.
Alba, Fruit-Localized Phytochromes Regulate Lycopene Accumulation Independently of Ethylene Production in Tomato. Plant Physiology 123:363-370, 2000.
Cantwell, Report to the California Tomato Commission: Tomato Variety Trials: Postharvest Evaluations for 2001.
Chen, A Rapid DNA Minipreparation Method Suitable for AFLP and Other PCR Applications. Plant Molecular Biology Reporter 17: 53-57, 1999.
Colbert, High-Throughput Screening for Induced Point Mutations. Plant Physiology 126:480-484, 2001.
Dhatt et al., Tomato Ripening Mutants—RIN, NOR and ALC: a Potential Germplasm to Improve Shelf Life, Veg. Sci. No. 29(1):1-12, 2002.
Edan, Color and Firmness Classification of Fresh Market Tomatoes. Journal of Food Science 62(4): 793-796, 1997.
Ernst, Structure of the Conserved Domain of ANAC, a member of the NAC family of transcription factors. EMBO Reports 5(3):297-303, 2004.
GenBank Accession No. AY573803 ([online], [retrieved on Mar. 22, 2013], retrieved from the internet (<http://www.ncbi.nlm.nih.gov/nuccore/AY573803>).
GenBank Accession No. AAU43922 ([online], [retrieved on Mar. 22, 2013], retrieved from the internet (<http://www.ncbi.nlm.nih.gov/protein/AAU43922>).
Henikoff, Using Substitution Probabilities to Improve Position-Specific Scoring Matrices. Computer Applications in the Biosciences 12:135-143, 1996.
Innis, PCR Protocols: A Guide to Methods and Applications. Academic Press, San Diego, 1990.
Lesage, Measurement of Tomato Firmness by Using a Non-Destructive Mechanical Sensor. Postharvest Biology and Technology 8:45-55, 1996.
Li, Integrated platform for detection of DNA Sequence Variants Using Capillary Array Electrophoresis. Electrophoresis 23(10):1499-1511, 2002.
McCallum, Target Screening for Induced Mutations. Nature Biotechnology 18:455-457, 2000a.
McCallum, Targeting Induced Local Lesions in Genomes (TILLING) for Plant Functional Genomics, Plant Physiology 123:439-442, 2000b.
Ng, Sift: Predicting Amino Acid Changes that Affect Protein Function. Nucleic Acids Research 31(13):3812-3814, 2003.

(Continued)

*Primary Examiner* — Elizabeth McElwain
*Assistant Examiner* — Charles Logsdon

(57) ABSTRACT

A series of independent human-induced, non-transgenic mutations found in at least one non-ripening (NOR) gene of tomato; tomato plants having these mutations in at least one of their NOR genes; and a method of creating and identifying similar and/or additional mutations in the NOR gene by screening pooled and/or individual tomato plants. The tomato plants of the present invention exhibit fruit that ripen more slowly, rot more slowly, are firmer, and have a longer shelf life post-harvest as a result of non-transgenic mutations in at least one of their NOR genes.

9 Claims, No Drawings

(56) References Cited

OTHER PUBLICATIONS

Olsen et al., NAC Transcription Factors: Structurally Distinct, Functionally Diverse. Trends in Plant Science, 10(2):79-97, 2005.
Saladie et al., A reevaluation of the key factors that influence tomato fruit softening and integrity, 144 Plant Phys., 1012-1028 (2007).
Stewart, A Rapid CTAB DNA Isolation Technique Useful for RAPD Fingerprinting and Other PCR Applications. Bio Techniques 14(5):748-749, 1993.
Taylor, Parsensp: A Tool for the Analysis of Nucleotide Polymorphisms. Nucleic Acids Research 31:3808-3811, 2003.

* cited by examiner

NON-TRANSGENIC TOMATO VARIETIES HAVING INCREASED SHELF LIFE POST-HARVEST

CROSS-REFERENCE TO RELATED APPLICATIONS

This application is a divisional of U.S. application Ser. No. 13/123,391 filed Apr. 8, 2011, which is a United States §371 National Phase application of PCT/US2009/060235, filed Oct. 9, 2009, both of which claim the benefit of U.S. Provisional Application No. 61/104,628, filed Oct. 10, 2008, all of which are hereby incorporated by reference in their entirety.

STATEMENT REGARDING FEDERALLY SPONSORED RESEARCH OR DEVELOPMENT

This invention was made with Government support under Contract No. W911QY-07-C-0121 awarded by the United States Department of Defense. The Government has certain rights in the invention.

FIELD OF THE INVENTION

This invention relates to novel human-induced, non-transgenic mutations of the non-ripening (NOR) gene of tomatoes and tomato plants having such non-transgenic mutations in at least one of their NOR gene sequences. This invention further relates to tomatoes that ripen more slowly, rot more slowly, are firmer, and have a longer shelf life post-harvest as a result of human-induced, non-transgenic mutations in at least one of their NOR genes. This invention also relates to a method that utilizes non-transgenic means to create tomatoes having mutations in at least one of their NOR genes.

BACKGROUND

One of the main challenges facing today's tomato industry is how to deliver to a processing plant or to the marketplace tomato fruit that have been vine-ripened (and thus are desirable to consumers in terms of taste, texture, and color), but that remain firm without the usual post-harvest ripening-related softening that reduces shelf life of harvested fruit. Using traditional breeding methods, which are very labor intensive, it could take years to develop a novel tomato variety that ultimately may display only a modest increase in shelf life. Instead, recent studies have utilized genetic and biochemical techniques in an effort to identify the factors that regulate fruit ripening. By identifying and modifying the expression of specific genes, researchers and breeders hope to develop new tomato varieties that have the desirable qualities of vine-ripened fruit, but that are resistant to post-harvest softening and therefore display an extended shelf life.

Ripening is a complex process involving numerous physiological and biochemical changes including changes in color, firmness, sugar content, and pathogen resistance. Post-harvest ripening limits the shelf life of fresh produce, such as tomatoes. Several genes involved in the ripening process have been identified by analysis of single locus mutations that result in a non-ripening phenotype. One of these genes has been called NOR after a naturally occurring mutation at the nor (non-ripening) locus of tomato. The non-ripening phenotype results from a 2 base pair deletion in the NOR gene, which causes a frame shift that affects NOR protein synthesis (see U.S. Pat. No. 6,762,347). This NOR deletion mutation severely impairs tomato fruit ripening and causes a broad range of undesirable traits that have proven difficult to eliminate through traditional breeding. It is the only characterized mutation in the NOR gene of tomato. NOR is a member of the NAC protein family, a large family of plant-specific transcription factors involved in multiple developmental processes, including formation of shoot apical meristem, floral organs, lateral shoots, hormone control and defense mechanisms, and programmed cell death. The structure of the DNA-binding NAC domain has recently been determined (Ernst et al., EMBO Reports 5(3):297-303, 2004; Olsen et al., Trends in Plant Science, 10(2):79-97, 2005).

Standard breeding methods have utilized the NOR deletion mutation in tomatoes (see U.S. Pat. No. 6,180,854). The usefulness of this deletion mutation is limited however since these mutant fruit fail to ripen normally. While the NOR deletion mutant fruit may have an increased shelf life, they have decreased sensory qualities (e.g., impaired flavor, aroma, and color) compared to wild type fruit which makes the nor deletion mutant fruit less appealing to consumers. Fruit that are homozygous for the NOR deletion mutation fail to ripen and remain hard and green. Breeders have attempted to use the NOR deletion mutation in the heterozygous state to develop firmer fruit. Even fruit that are heterozygous for the NOR deletion mutation fail to fully develop the red color and sensory qualities that consumers desire in ripened fruit.

To date, other useful characterized mutations in the NOR gene of tomato are not available. Because NOR exerts pleiotropic effects, it would be useful to have an allelic series of mutations in the NOR gene that provide a spectrum of firmness and color phenotypes that could be used to optimize the breeding of extended shelf life tomato varieties that retain many of the quality traits of vine-ripened tomatoes. Additional useful NOR mutations would include those that increase shelf life but do not affect flavor, aroma and color as adversely as the naturally occurring nor deletion mutation. Tomato lines with NOR mutations that have been genetically characterized could also be crossed with lines that carry mutations in other genes involved in ripening.

In addition to standard breeding methods utilizing the nor mutation, transgenic approaches that targeted the NOR gene (see U.S. Pat. No. 6,762,347; U.S. Patent Application No. 20050076410) have been proposed for tomato fruit development. However, public acceptance of genetically modified plants, particularly with respect to plants used for food, is not universal. Because a cultivated tomato that is resistant to post-harvest softening and has improved shelf life with quality traits acceptable to consumers would be useful, an allelic series of novel mutations in the NOR gene of tomato were created. A cultivated tomato with reduced fruit softening as a result of altered NOR that was not the result of genetic engineering would have tremendous value for the tomato industry, including fresh market tomatoes, processor tomatoes and tomato food products such as sliced tomatoes, canned tomatoes, ketchups, soups, sauces, juices and pastes.

SUMMARY OF THE INVENTION

In accordance with one exemplary embodiment, this invention includes a tomato plant having tomato fruit with increased firmness, reduced rot rate, and increased shelf life post-harvest compared to wild type tomato fruit due to a human-induced, non-transgenic mutation in the NOR gene, as well as fruit, seeds, pollen, plant parts and progeny of that plant.

In accordance with another exemplary embodiment, this invention includes a tomato plant having tomato fruit that ripen more slowly post-harvest compared to wild type tomato fruit due to a human-induced non-transgenic mutation in the NOR gene, as well as fruit, seeds, pollen, plant parts and progeny of that plant.

In accordance with another exemplary embodiment, this invention includes food and food products incorporating tomato fruit having increased firmness, reduced rot rate, and increased shelf life post-harvest caused by a human-induced non-transgenic mutation in the NOR gene.

In accordance with yet another exemplary embodiment, this invention includes a tomato plant having fruit with increased shelf life compared to wild type tomato fruit created by the steps of obtaining plant material from a parent tomato plant, inducing at least one mutation in at least one copy of a NOR gene of the plant material by treating the plant material with a mutagen to create mutagenized plant material, culturing the mutagenized plant material to produce progeny tomato plants, analyzing progeny tomato plants to detect at least one mutation in at least one copy of a NOR gene, selecting progeny tomato plants that have fruit with extended shelf life compared to the parent tomato plant; and repeating the cycle of culturing the progeny tomato plants to produce additional progeny plants having extended shelf life.

BRIEF DESCRIPTION OF THE SEQUENCE LISTING

SEQ ID NO: 1 shows a Solanum lycopersicum NAC domain protein (NAC-NOR) gene, NAC-NOR-NOR allele, complete cds (NCBI Accession Number AY573803).

SEQ ID NO: 2 shows the protein encoded by SEQ ID NO: 1 (NCBI Accession Number AAU43922).

SEQ ID NOs: 3-8 show the DNA sequences for the Solanum lycopersicum NOR specific PCR primers used to detect the mutations of the present invention.

A substitute sequence listing is herein incorporated by reference to the material contained in the associated file, entitled, "substitutesequencelist.txt," submitted herewith, created on Apr. 5, 2011, and comprising 8.72 kb in size.

DETAILED DESCRIPTION OF PREFERRED EMBODIMENTS

In accordance with one exemplary embodiment, the present invention provides tomatoes that have an extended shelf life as compared to wild type tomatoes due to a mutation in at least one of their NOR genes and without the inclusion of foreign nucleic acids in the tomatoes' genomes. In accordance with other exemplary embodiments, the present invention provides a series of independent non-transgenic mutations in the NOR gene; tomatoes having these mutations in at least one of their NOR genes; and a method of creating and identifying similar and/or additional mutations in the NOR gene of tomatoes.

In order to create and identify the NOR mutations and tomatoes of the present invention, the present inventors utilized a method known as TILLING. See McCallum et al., Nature Biotechnology 18:455-457, 2000; McCallum et al., Plant Physiology 123:439-442, 2000; Colbert et al., Plant Physiology 126:480-484, and U.S. Pat. No. 5,994,075 and U.S. Publication No. 20040053236, all of which are incorporated herein by reference. In the basic TILLING methodology, plant material, such as seed, is subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of tomato having at least one NOR gene with substantial homology to SEQ ID NO: 1 may be used in accordance with the present invention. As used herein, "substantial homology" means that the DNA sequence of the gene is sufficiently similar to SEQ ID NO: 1 at the nucleotide level to code for the equivalent protein as SEQ ID NO: 1, allowing for allelic differences between cultivars. In accordance with one aspect of an exemplary embodiment of the invention, "substantial homology" may be present when the homology between the NOR gene and SEQ ID NO: 1 is as low as about 85%, provided that the homology in the conserved regions of the gene is higher (e.g., at least about 90%). Preferably, the percent identity in the coding region is 85-90%, more preferably 90-95%, and optimally, it is above 95%. One of skill in the art may prefer a tomato cultivar having commercial popularity or one having specific desired characteristics in which to create the NOR-mutated tomatoes. Alternatively, one of skill in the art may prefer a tomato cultivar having few polymorphisms, such as an in-bred cultivar, in order to facilitate screening for mutations within the NOR loci.

In accordance with one aspect of an exemplary embodiment of the present invention, seeds from tomatoes were mutagenized and then grown into M1 plants. The M1 plants were then allowed to self-pollinate and seeds from the M1 plant were grown into M2 plants, which were then screened for mutations in their NOR locus. While M1 plants may be screened for mutations, an advantage of screening the M2 plants is that all somatic mutations correspond to the germline mutations. One of skill in the art would recognize that a variety of tomato plant materials, including, but not limited to, seeds, pollen, plant tissue or plant cells, may be mutagenized in order to create the NOR-mutated tomatoes of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for NOR mutations instead of waiting until the M2 generation.

Mutagens that create primarily point mutations and short deletions, insertions, transversions, and or transitions (about 1 to about 5 nucleotides), such as chemical mutagens or radiation, may be used to create the mutations of the present invention. Mutagens conforming with the method of the present invention include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino]acridine dihydrochloride (ICR-170), and formaldehyde. Spontaneous mutations in NOR that may not have been directly caused by the mutagen can also be identified in accordance with various embodiments of the present invention.

Any suitable method of plant DNA preparation now known or hereafter devised may be used to prepare the tomato plant DNA for NOR mutation screening. For example, see Chen and Ronald, Plant Molecular Biology Reporter 17:53-57, 1999; Stewart and Via, Bio Techniques 14:748-749, 1993. Additionally, several commercial kits are available, including kits from Qiagen (Valencia, Calif.) and Qbiogene (Carlsbad, Calif.).

In accordance with one aspect of an exemplary embodiment of the invention, DNA samples from individual tomato plants are prepared and then pooled in order to expedite screening for mutations in NOR of the entire population of plants originating from the mutagenized plant tissue. The size of the pooled group may be dependent upon the sensitivity of the screening method used. In accordance with one aspect of an exemplary embodiment of the invention, groups of four or more individual tomato plants are pooled.

In accordance with another aspect of an exemplary embodiment, after the DNA samples are pooled, the pools are subjected to NOR sequence-specific amplification techniques, such as Polymerase Chain Reaction (PCR). For a general overview of PCR, see PCR Protocols: A Guide to Methods and Applications (Innis, Gelfand, Sninsky, J., and White, eds.), Academic Press, San Diego, 1990. Any primer specific to the NOR locus or the sequences immediately adjacent to the NOR locus may be utilized to amplify the NOR sequences within the pooled DNA sample. Preferably, the primer is designed to amplify the regions of the NOR locus where useful mutations are most likely to arise. Most preferably, the primer is designed to detect mutations in the coding region of the NOR gene. Additionally, it is preferable for the primer to avoid known polymorphic sites in order to ease screening for point mutations. To facilitate detection of PCR products on a gel, the PCR primer may be labeled using any conventional or hereafter devised labeling method.

Exemplary primers (SEQ ID NOs: 3-8) that have proven useful in identifying useful mutations within the NOR sequence are shown below in Table 1. These primers are also detailed in the Sequence Listing appended hereto.

TABLE 1

PCR primers specific for the NOR gene in tomato.

| SEQ ID | PRIMER NAME | SEQUENCE |
| --- | --- | --- |
| 3 | NORA-3193 | tgaattcaggtcaactcaaacatc gtaaattg |
| 4 | NORA-3194 | aattcacttttacacgttatcgt ggatatcttttg |
| 5 | NORB-3195 | aaagtagtggacaaacataaagta gtggacccataa |
| 6 | NORB-3196 | tgaaagttgaatcaagtcatctac aacaacaaca |
| 7 | NORC-3235 | aatgaaaatcctgaatcggccact aactttaac |
| 8 | NORC-3236 | atgattgattgatcgattgatttt acagggcta |

In accordance with one aspect of an exemplary embodiment of the invention, the PCR amplification products may be screened for NOR mutations using any method that identifies nucleotide differences between wild type and mutant sequences. These may include, without limitation, sequencing, denaturing high pressure liquid chromatography (dH-PLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al., Plant Physiology 126:480-484, 2001. Preferably, the PCR amplification products are incubated with an endonuclease that preferentially cleaves mismatches in heteroduplexes between wild type and mutant sequences. In accordance with another aspect of an exemplary embodiment, cleavage products are electrophoresed using an automated sequencing gel apparatus, and gel images are analyzed with the aid of a standard commercial image-processing program.

The present inventors have determined that to achieve reduced post-harvest softening in tomatoes, mutations that alter NOR function are desirable. Preferred mutations include missense, nonsense and splice junction changes, including mutations that prematurely truncate the translation of the NOR protein from messenger RNA, such as those mutations that create a stop codon within the coding regions of the NOR gene. Such mutations include insertions, repeat sequences, modified open reading frames (ORFs) and, most preferably, point mutations.

In accordance with yet another aspect of an exemplary embodiment of the invention, once an M2 plant having a mutated NOR sequence is identified, the mutations are analyzed to determine its affect on the expression, translation, and/or activity of the protein. In accordance with one exemplary embodiment, the PCR fragment containing the mutation is sequenced, using standard sequencing techniques, in order to determine the exact location of the mutation in relation to the overall NOR sequence. Each mutation is evaluated in order to predict its impact on protein function (i.e., completely tolerated to loss-of-function) using bioinformatics tools such as SIFT (Sorting Intolerant from Tolerant; Ng et al., Nucleic Acids Research 31:3812-3814, 2003), PSSM (Position-Specific Scoring Matrix; Henikoff and Henikoff, Computer Applications in the Biosciences 12:135-143, 1996) and PARSESNP (Taylor and Greene, Nucleic Acids Resarch 31:3808-3811, 2003). For example, a SIFT score that is less than 0.05 and a large change in PSSM score (e.g., roughly 10 or above) indicate a mutation that is likely to have a deleterious effect on protein function.

In accordance with a further aspect of an exemplary embodiment, if the initial assessment of a mutation in an M2 plant indicates it to be of a useful nature and in a useful position within the NOR gene, then further phenotypic analysis of the tomato plant containing that mutation is pursued. First, the M2 plant is backcrossed or outcrossed twice to create a BC1 plant in order to eliminate background mutations. Then the backcrossed or outcrossed BC1 plant is self-pollinated in order to create a BC1F2 plant that is homozygous for the NOR mutation.

Several physical characteristics of these homozygous NOR mutant plants are assessed to determine if the mutation results in a useful phenotypic change in the tomato. Mutant NOR tomatoes are evaluated post-harvest for several traits including rate of ripening, firmness, rot rate and shelf life compared to normal (e.g., wild type) parental tomatoes or to wild type sibling control tomatoes. Evaluations can be performed during storage. Examples of standard storage conditions include room temperature storage (approximately 68° F./20° C.) or refrigerated storage (approximately 55° F./13° C.). Normal fruit ripens on the vine or during storage such that the color of the tomato changes from light green to red. As this change occurs, the fruit tends to become softer such that compression under a specified weight becomes greater and/or the force required to depress the surface of the fruit a specified distance becomes less. See Cantwell, Report to the California Tomato Commission: Tomato Variety Trials: Postharvest Evaluations for 2001; Edan et al., J. Food Science 62(4): 793-796, 1997; Errington et al., Postharvest Biology and Technology 11: 141-147, 1997; Lesage and Destain, Postharvest Biology and Technology 8: 45-55, 1996. For lycopene measurements, see Alba et al., Plant Physiology 123:363-370, 2000.

The following novel mutations identified in Table 2 are exemplary of the mutations created and identified according to various embodiments of the present invention. The only previously reported mutation in the NOR gene—the nor two base pair deletion mutation (U.S. Pat. No. 6,762,347)—results in a frameshift beginning at the glutamine at amino acid 183 according to SEQ ID NO: 2 that ends in a truncation (stop*) four amino acids later (QRSID to QVHR*).

TABLE 2

Examples of novel mutations created and identified in the NOR gene of tomato.

| Type of Mutation | Variety | Primer SEQ IDs. | EMS Treatment | Nucleotide Mutation According to SEQ ID NO: 1 | Amino Acid (a.a.) Mutation According to SEQ ID NO: 2 | Amino Acid (a.a.) Mutation According to SEQ ID NO: 2 |
|---|---|---|---|---|---|---|
| Missense | Shady Lady | B | 0.8% | G995A | G68E | glycine to glutamic acid at a.a. 68 |
| Missense | NC84173 | B | 1.2% | G1048A | A86T | alanine to threonine at a.a. 86 |
| Truncation (stop) | NC84173 | C | 1.2% | C2277T | Q206* | glutamine to stop at a.a. 206 |
| Missense | NC84173 | C | 1.2% | G2425A | G255D | glycine to aspartic acid at a.a. 255 |
| Truncation (stop) | Shady Lady | C | 0.8% | G2434A | W258* | tryptophan to stop at a.a. 258 |
| Missense | Shady Lady | C | 0.6% | G2646C | E329Q | glutamic acid to glutamine at a.a. 329 |
| Missense | NC84173 | C | 1.2% | G2673T | G338W | glycine to tryptophan at a.a. 338 |

The nomenclature used in the Table 2 indicates the wild type nucleotide or amino acid, followed by its position according to the referenced SEQ ID NO, followed by the changed nucleotide or amino acid at that position using standard genetic code terminology (see specific examples below).

The following Examples are offered by way of illustration only, and not limitation. It is to be understood that the mutations below are merely exemplary and that similar mutations are also contemplated.

EXAMPLE 1

Mutagenesis

In one embodiment of the present invention, tomato seeds of cultivars Shady Lady (hybrid) and NC84173 were vacuum infiltrated in $H_2O$ (approximately 1,000 seeds/100 ml $H_2O$ for approximately 4 minutes). The seeds were then placed on a shaker (45 rpm) in a fume hood at ambient temperature. The mutagen ethyl methanesulfonate (EMS) was added to the imbibing seeds to final concentrations ranging from about 0.1% to about 1.6% (v/v) in accordance with one aspect of an exemplary embodiment of the invention. Following a 6 to 24-hour incubation period, the EMS solution was replaced 4 times with fresh $H_2O$. The seeds were then rinsed under running water for approximately 1 hour. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from these M2 plants produced in accordance with the above description was extracted and prepared in order to identify which M2 plants carried a mutation at their NOR loci. The M2 plant DNA was prepared using the methods and reagents contained in the Qiagen (Valencia, Calif.) DNeasy 96 Plant Kit. Approximately 50 mg of frozen plant sample was placed in a sample tube with a tungsten bead, frozen in liquid nitrogen and ground 2 times for 1 minute each at 20 Hz using the Retsch Mixer Mill MM 300. Next, 400 μl of solution AP1 [Buffer AP1, solution DX and RNAse (100 mg/ml)] at 80° C. was added to the sample. The tube was sealed and shaken for 15 seconds. Following the addition of 130 μl Buffer AP2, the tube was shaken for 15 seconds. The samples were placed in a freezer at minus 20° C. for at least 1 hour. The samples were then centrifuged for 20 minutes at 5,600X g. A 400 μl aliquot of supernatant was transferred to another sample tube. Following the addition of 600 μl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600X g. Next, 800 μl of Buffer AW was added to each well of the filter plate, sealed and spun for 15 minutes at 5,600X g in the square well block. The filter plate was then placed on a new set of sample tubes and 80 μl of Buffer AE was applied to the filter. It was capped and incubated at room temperature for 1 minute and then spun for 2 minutes at 5,600X g. This step was repeated with an additional 80 μl Buffer AE. The filter plate was removed and the tubes containing the pooled filtrates were capped. The individual samples were then normalized to a DNA concentration of 5 to 10 ng/µl.

Tilling

The M2 DNA was pooled into groups of four individuals. The DNA concentration for each individual within the pool was 0.25 ng/µl with a final concentration of 1 ng/µl for the entire pool. The pooled DNA samples were arrayed on microtiter plates and subjected to gene-specific PCR.

PCR amplification was performed in 15 µl volumes containing 2.5 ng pooled DNA, 0.75X ExTaq buffer (Panvera®, Madison, Wis.), 2.6 mM $MgCl_2$, 0.3 mM dNTPs, 0.3 µM primers, and 0.05U Ex-Taq (Panvera) DNA polymerase. PCR amplification was performed using an MJ Research thermal cycler as follows: heat denaturation at 95° C. for 2 minutes; followed by 8 cycles of "touchdown PCR" (94° C. for 20 seconds, followed by an annealing step starting at 68-70° C. for 30 seconds and decreasing 1° C. per cycle, then a temperature ramp increasing 0.5° C. per second to 72° C., and followed by 72° C. for 1 minute); then 25-45 more cycles of PCR (94° C. for 20 seconds, 61-63° C. for 30 seconds, a ramp increasing 0.5° C. per second up to 72° C., 72° C. for 1 minute); and finally extension, denaturation and re-annealing steps (72° C. for 8 minutes; 98° C. for 8 minutes; 80° C. for 20 seconds; followed by 60 cycles of 80° C. for 7 seconds decreasing 0.3° C. per cycle).

The PCR primers (MWG Biotech, Inc., High Point, N.C.) were mixed as follows:

9 µl 100 µM IRD-700 labeled left primer
1 µl 100 µM left primer
10 µl 100 µM right primer The IRD-700 label can be attached to either the right or left primer. Preferably, the labeled to unlabeled primer ratio is 9:1. Alternatively, Cy5.5 modified primers or IRD-800 modified primers could be used. Additionally, both primers could be labeled simultaneously with distinguishable labels such as IRD-700 and IRF-800. In the present invention, the IRD-700 label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton X-100, 20 ng/ml of bovine serum albumin, and CEL 1 (Transgenomic, Inc.; 1:100,000 dilution) was added with mixing on ice, and the plate was incubated at 45° C. for 15 min. The specific activity of the CEL 1 was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at 80° C., spun at 4,000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 hours at 1,500-V, 40-W, and 40-mA limits at 50° C.

During electrophoresis, the gel was imaged using a LI-COR (Lincoln, Nebr.) scanner, which was set at a channel capable of detecting the IR Dye 700 label. The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation).

Physical and Biochemical Measurements

Tomatoes Selected for Study

Individual tomatoes selected for study were picked from plants derived from siblings of the same cross to preserve background phenotypes as much as possible. The plants and fruit were genotyped as homozygous for the mutation, heterozygous for the mutation, or wild type. Genotyping was performed using Taqman SNP Genotyping Assays (Applied Biosystems) to discriminate the three different alleles of the NOR locus.

Evaluation of Sensory Qualities

In general, tomato fruit that had one or more mutant alleles in NOR were similar in sensory qualities to wild type control tomatoes, though the attainment of full flavor, color and aroma was delayed in tomatoes with NOR mutations due to their delayed ripening. This is an improvement over fruit with the original NOR deletion mutation described in U.S. Pat. No. 6,762,347, which fail to fully develop the sensory qualities associated with ripe fruit. For example, fruit that were heterozygous for the W258* mutation were compared to wild type control fruit in a blind taste test. Tomatoes were stored at approximately 40° F. (4° C.) and approximately 55° F. (13° C.) and evaluated every two weeks. Results showed that W258* heterozygous tomatoes were as acceptable in odor, quality of flavor-point balance, texture attributes and overall quality as wild type control fruit. W258* heterozygous tomatoes were found to be superior to wild type tomatoes at 40° F. (4° C.). At 55° F. (13° C.), taste testers ranked W258* heterozygous tomatoes as under ripe at 2 weeks, fully ripe at 4 weeks, and slightly over ripe at 6 weeks post-harvest, whereas they ranked wild type control tomatoes as fully ripe at 2 weeks and over ripe at 4 and 6 weeks. Thus, W258* heterozygous tomatoes developed the full sensory profile and retained more quality over time than wild type control tomatoes.

Measurement of Fruit Firmness

Fruit (homozygous, heterozygous, and/or wild type siblings) were harvested at breaker stage and allowed to ripen at room temperature to light red stage. After the light red stage, tomatoes were stored at 55° F. (13° C.). Firmness was measured using a model TA-XT Texture Analyzer (Texture Technologies, Scarsdale, N.Y.). The amount of force required to depress the tomato fruit surface 5 mm was recorded for each sample. Fruit firmness was measured twice for each fruit, equatorially, at two time points. The first two measurement locations were marked on the fruit, and subsequent measurements were taken at least 7 days later at different equatorial locations. Thus, each fruit was depressed four times. In general, time points were 7 days or increments of 7 days apart. In general, tomato fruit that had one or more mutant alleles in NOR were more firm than wild type control fruit. Exemplary data from measurements at 21 or 28 days post-harvest at shown in Table 3.

TABLE 3

Exemplary data from measurement of fruit firmness. Data are expressed in Newtons.

| Mutation | Genotype | Sample Size | Firmness After 21 Days in Storage (X ± SEM) | Firmness After 28 Days in Storage (X ± SEM) |
|---|---|---|---|---|
| G68E | HOM | n = 14 | 11.6 ± 0.95 | — |
|  | WT | n = 8 | 9.7 ± 0.92 | — |
| Q206* | HOM | n = 3 | — | 38.7 ± 1.58 |
|  | HET | n = 3 | — | 12.0 ± 0.42 |
|  | WT | n = 3 | — | 10.3 ± 1.95 |
| W258* | HOM | n = 11 | 20.3 ± 1.63 | — |
|  | HET | n = 33 | 11.6 ± 0.38 | — |
|  | WT | n = 22 | 8.8 ± 0.30 | — |

Measurement of Rot Rate

Fruit for each genotype were harvested at the breaker stage of fruit development and ripened to red prior to commencing the study to ensure that tomatoes of each type were at the same physiological age. Tomatoes were stored at approximately 55° F. (13° C.) and evaluated on a weekly basis for signs of rot. The rot rate was then calculated over time as the percent of tomatoes exhibiting rot, and the number of days in storage until all fruit had rotted was recorded. The rot rate was then used to extrapolate the number of days at which 50% of the fruit showed signs of rot. Using both data points eliminates the effect of outliers and illustrates the progression of rot. Fruit homozygous for NOR mutations were compared to fruit that were heterozygous for the NOR mutations and/or wild type sibling controls.

In general, tomato fruit that had one or more mutant alleles in NOR showed a reduced rate of rot and increased shelf life compared to wild type control fruit. Exemplary data for rot rate in three mutant lines are shown in Table 4.

TABLE 4

Exemplary data of measurement of rot rate.

| Mutation | Genotype | Sample Size | Days in Storage Until 50% of Fruit Rot | Days in Storage Until 100% of Fruit Rot |
|---|---|---|---|---|
| G68E | HOM | n = 14 | 56 | 75 |
|  | WT | n = 8 | 34 | 61 |
| Q206* | HOM | n = 3 | >90 | >90 |
|  | HET | n = 3 | 31 | 75 |
|  | WT | n = 3 | 23 | 50 |
| W258* | HOM | n = 11 | 72 | 75 |
|  | HET | n = 33 | 58 | 75 |
|  | WT | n = 22 | 31 | 43 |

Evaluation of Color

Tomato fruit color was measured analytically using a Minolta CR-400 Chromameter. The a* values from the CIE L*a*b* color space measurements generated by the instrument were used to provide quantitative values for degree of ripening from green to red. The a* spectrum is the part of the CIE L*a*b* color space that defines the green (negative a*) to red (positive a*) color of any sample. For our purposes, the a* values specifically define the developmental stage of the fruit of red-fruited tomato cultivars. Tomatoes are considered to be ripe at the light red stage of development when the a* values are >20. Tomatoes at the pink stage of development have values between 10 and 20. Turning tomatoes have values between 0 and 10 and breaker and mature green tomatoes have negative a* values.

Of the seven mutations examined, all except but one (Q206*) achieved a maximum color of light pink to red. One particularly useful mutation is G68E. Tomatoes that are homozygous for the G68E allele are firmer than wild type tomatoes (11.6 versus 9.7) and have a reduced rate of rot compared to wild type controls (21 and 14 days longer in storage before reaching rot rates of 50% and 100%, respectively). Surprisingly, the G68E homozygous tomatoes attained an equivalent red color under 55° F. (13° C.) storage. Exemplary data for measurement of color are shown in Table 5.

TABLE 5

Exemplary data for measurement of color.

| Mutation | Genotype | Sample Size | Maximum Color Stored at 55° F. (13° C.) | Maximum Color Stored at 68° F. (20° C.) |
|---|---|---|---|---|
| G68E | HOM | n = 14 | 29.1 | — |
|  | WT | n = 8 | 27.5 | — |
| Q206* | HOM | n = 3 | 0.5 | — |
|  | HET | n = 3 | 22.9 | — |
|  | WT | n = 3 | 29.6 | — |
| W258* | HOM | n = 11 | 17.1 | 4.3 |
|  | HET | n = 33 | 29 | 30.6 |
|  | WT | n = 22 | 29.3 | — |

Identification and Evaluation of Mutation G68E

DNA from a tomato originating from seeds of cultivar Shady Lady that were incubated in 0.8% EMS was amplified using primers NORB-3195 and NORB-3196 (SEQ ID NOs: 5 and 6). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in a NOR sequence. Sequence analysis of this fragment showed the mutation was a G to A change at nucleotide 995 of SEQ ID NO: 1. This mutation correlates with a change from glycine to glutamic acid at amino acid 68 of the NOR protein [SEQ ID NO: 2].

Tomatoes homozygous for the G68E mutation in their NOR gene ripen more slowly, rot more slowly, are firmer and display a longer shelf life post-harvest than wild type sibling control tomatoes and have improved color compared to the original NOR deletion mutant described in U.S. Pat. No. 6,762,347. Tomatoes heterozygous for the G68E mutation in their NOR gene display a ripening rate that is intermediate between the homozygous and wild type controls.

Identification and Evaluation of Mutation Q206*

DNA from a tomato originating from seeds of cultivar NC84173 that were incubated in 1.2% EMS was amplified using primers NORC-3235 and NORC-3236 (SEQ ID NOs: 7 and 8). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in a NOR sequence. Sequence analysis of this fragment showed the mutation was a C to T change at nucleotide 2277 of SEQ ID NO: 1. This mutation correlates with a change from glutamine at amino acid 206 of the NOR protein [SEQ ID NO: 2] to a stop codon.

Tomatoes homozygous for the Q206* mutation in their NOR gene reach the Breaker stage of fruit development, which indicates an initiation of the ripening process. This observation differs from the original NOR deletion mutation described in U.S. Pat. No. 6,762,347 where fruit do not initiate ripening at all. In the heterozygous state, this mutation ripens to the pink stage of development and fruit rot more slowly, are firmer and display a longer shelf life post-harvest than wild type sibling control tomatoes.

Identification and Evaluation of Mutation W258*

DNA from a tomato originating from seeds of cultivar Shady Lady that were incubated in 0.8% EMS was amplified using primers NORC-3235 and NORC-3236 (SEQ ID NOs: 7 and 8). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in a NOR sequence. Sequence analysis of this fragment showed the mutation was a G to A change at nucleotide 2434 of SEQ ID NO: 1. This mutation correlates with a change from tryptophan at amino acid 258 of the NOR protein [SEQ ID NO: 2] to a stop codon.

Tomatoes homozygous for the W258* mutation in their NOR gene ripen more slowly, rot more slowly, are firmer and display a longer shelf life post-harvest than wild type sibling control tomatoes and have improved color when allowed to ripen at 55° F. (13° C.) compared to the original NOR deletion mutant described in U.S. Pat. No. 6,762,347. Tomatoes that are heterozygous for the W258* mutation in their NOR gene display an intermediate phenotype between homozygous and wild type tomatoes and thus ripen more slowly, rot more slowly, are firmer and display a longer shelf life post-harvest than wild type sibling control tomatoes, but unlike the homozygous tomatoes, these tomatoes ripen fully.

The above examples are provided to illustrate exemplary embodiments of the present invention but not limit its scope. Other variants of the invention will be readily apparent to one of ordinary skill in the art and are encompassed by the appended claims and all their equivalents. All publications, patents, and patent applications cited herein are hereby incorporated by reference.

The invention claimed is:

1. A non-ripening (NOR) gene from tomato comprising a human-induced, non-transgenic G995A mutation; wherein said human-induced, non-transgenic G995A mutation comprises a nucleotide change within the NOR gene; wherein said nucleotide change is identified according to SEQ ID NO: 1; and wherein said NOR gene codes for a protein having the amino acid sequence of SEQ ID NO: 2 with a single amino acid change.

2. A tomato plant containing a human-induced, non-transgenic mutation within its NOR. gene; wherein said human-induced, non-transgenic mutation is G995A; wherein said human-induced, non-transgenic mutation comprises a nucleotide change within the NOR gene; and wherein said nucleotide change is identified according to SEQ ID NO: 1.

3. A fruit, a seed, a pollen grain, a plant part, or the progeny of the tomato plant of claim 2; wherein the fruit, the seed, the pollen grain, the plant part, or the progeny comprises the mutation.

4. A food or a food product comprising the fruit of claim 3.

5. The tomato plant of claim 2, wherein expression of said mutation in the homozygous state results in fruit that are firmer than wild type fruit and turn pink when ripened at standard storage conditions.

6. A NOR protein from tomato comprising a G68E amino acid change; wherein said amino acid change results from a human-induced non-transgenic mutation in the NOR gene; wherein said amino acid change is identified according to SEQ ID NO: 2; and wherein said NOR protein has, apart from said amino acid change, complete identity to SEQ ID NO: 2.

7. A tomato fruit comprising the NOR protein of claim 6.

8. A food or a food product comprising the tomato fruit of claim 7.

9. The tomato fruit of claim 7, wherein expression of said amino acid change in its NOR protein in the homozygous state results in fruit that are firmer than wild type fruit and turn pink when ripened at standard storage conditions.

* * * * *

SEQUENCE LISTING

```
<160> NUMBER OF SEQ ID NOS: 8

<210> SEQ ID NO 1
<211> LENGTH: 2885
<212> TYPE: DNA
<213> ORGANISM: Lycopersicum esculentum
<300> PUBLICATION INFORMATION:
<308> DATABASE ACCESSION NUMBER: AY573803
<309> DATABASE ENTRY DATE: 2004-03-16
<313> RELEVANT RESIDUES IN SEQ ID NO: (1)..(2885)

<400> SEQUENCE: 1
ctaaattcct tcttgtttat cattttctct cttcccaaaa aaaaatccca aaatttaatc      60
ataatacaat tcgaatttat caacctcgta ctacgtacat attttttgttg gtacgtaaaa     120 tactgaattc aggtcaactc aaacatcgta aattgtgatt tctttatgga aagtacggat     180
tcatcaaccg ggacacgtca tcagcctcaa ctcccaccgg ggtttcgatt ccacccgacg     240
gacgaagaac tcatcgtcca ctacctcaaa aaacgagtcg ccggcgctcc gattccggtg     300
gatattattg gtgaaattga tctttataag tttgatccat gggaactccc tgctactatt     360
ttcaccacta tactatattt tcttgcccta taacttatat atagggaaa aagatcggag      420 tcagcgatga acaattattg tgtctaaatt aaattttaaa tatgcaatag attggtgacg     480
aatttcgttg ctaattaatt ttttagtgat aaattaatat ttttcccctt tttaatcttc     540
atgtttttta tcacaaagtt ttctatgacc aactyataaa gatttgaact cgatcaattt     600
tttttttaga atgaatgaac ttatgttata tatagtgata ttttaaatgc ttttttatat     660
tttcaaaaga tatccacgat aacgtgtaaa aagtgaattt gcaaaaaaaa aatgtagtac     720
cttttattta attttattgt agataattta gattttaatt ttgaatttgt ttaatttaaa     780
ttctgaatcg tataatattt atttaatttc tatttttga gtttttttt ggagggtgct      840 taaaaagtag tattcacaaa tataaagtag tggacaaaca taaagtagtg gacccataat     900
ttattttttt aaaaattata ttaaaactat ttgttaagtt taaattctga attatcttct     960
tatcatgtgt ttaacgcagc taaggcaata ttcggagagc aagaatggtt cttttttagt    1020
ccaagagata gaaaatatcc taacggggcg aggccaaatc gggctgcaac atcggttat    1080 tggaaggcta ccggaaccga caagccggtt tttacttccg gtggaacaca aaaggttggg    1140
gtaaaaaagg cgctcgtttt ttacggcggt aaaccaccaa aaggggtaaa aactaattgg    1200
atcatgcatg aatacagagt tgtagaaaat aaaacaaata acaagccact tggttgtgat    1260
```

-continued

```
aatattgttg ccaacaaaaa aggatctttg agggtaagtc ctaaattttg catcgaaact    1320
aatttctcta tcgtatcaga tagggataag atatacgtat actctaatct ccttgaacca    1380
cacaagtact atactagata tgttgttgtt gtagatgact tgattcaact ttcaaatttt    1440
tgatgaaaat gtttaagtta tatataccat atatatatag gcgtagctaa aaatttcgat    1500 aaggggttt aaatctgaaa aaatggatat acgaaatagc cgaaagaggt tcgacataga     1560
ttattttaac catataaaaa taatacaatt ttcatatata tatacgccgt ggttaatatg    1620
aggaatattt tatactatta atgtacttta accaggggcg gctctagagt tgatgaaccc    1680
tctcagcgaa aatttacgtt gtatatttaa ggtaccttt aataattttt gtatttatat     1740
attaattttg aacctcttga atataagatt agacgttgac ttagtggttt caggggttca    1800
aatcactatt cttttttcc taacccccctt aatgaaaatc ctgaatcggc cactaacttt    1860
aactggttat agaaggttaa tcttactaga aaaaagcatg aaattctaac cgacaaagat    1920
gtagtcgccc agtagataa aacgtttaaa ttgggcggat agagttactt tattttttcac    1980 tgtcatatgt tactatatat tgacacttca cttaaagagt tatcatatcg atattttttac   2040 tattagtgta cataacacaa actcgaataa attcaatgtt tcattagcta gttaattagt    2100 ctaactttt taaaaaaaaa tattttttctt actccacact atttttatttt attttttttgc   2160 agctagatga ttgggtttta tgtcgaattt acaagaagaa taacacacaa aggtccatag    2220
atgatttgca tgatatgttg ggatcgatac cacaaaatgt accaaattca atattacaag    2280
gaataaagcc ttcaaactat ggtacaatat tgctcgaaaa tgaatcgaat atgtacgatg    2340
gaattatgaa taacacgaac gatattatca acaataataa tagatccatt ccacaaatat    2400
cgtcaaagag aacgatgcat ggaggtttgt attggaataa cgacgaagca acaacaacaa    2460
caacaactat tgataggaac cattctccaa atacaaaaag gttccttgtt gagaacaacg    2520
aggacgatgg acttaacatg aataatattt cgcgaattac aaatcatgaa caaagtagct    2580
ccattgccaa tttcctgagc cagtttcctc aaaatccttc gattcaacaa caacaacaac    2640
aacaagaaga agtattggga tctcttaatg atggggtcgt cttttcgacaa ccttataatc    2700 aagttactgg catgaattgg tactcttaaa gatataaaaa ggcaaaaaat agttagccct    2760
gtaaaatcaa tcgatcaatc aatcatagat atattatata tggatttcgt tatattttac    2820
ttttagttag aattaatata tagaatatct tctatctcac attaacaaat aagaacattt    2880
ataac                                                                2885
```

<210> SEQ ID NO 2
<211> LENGTH: 355
<212> TYPE: PRT
<213> ORGANISM: Lycopersicum esculentum
<300> PUBLICATION INFORMATION:
<308> DATABASE ACCESSION NUMBER: AAU43922
<309> DATABASE ENTRY DATE: 2004-03-16
<313> RELEVANT RESIDUES IN SEQ ID NO: (1)..(355)

<400> SEQUENCE: 2

```
Met Glu Ser Thr Asp Ser Ser Thr Gly Thr Arg His Gln Pro Gln Leu
1               5                   10                  15

Pro Pro Gly Phe Arg Phe His Pro Thr Asp Glu Glu Leu Ile Val His
            20                  25                  30

Tyr Leu Lys Lys Arg Val Ala Gly Ala Pro Ile Pro Val Asp Ile Ile
        35                  40                  45

Gly Glu Ile Asp Leu Tyr Lys Phe Asp Pro Trp Glu Leu Pro Ala Lys
```

```
            50                  55                  60
Ala Ile Phe Gly Glu Gln Glu Trp Phe Phe Ser Pro Arg Asp Arg
 65                  70                  75                  80

Lys Tyr Pro Asn Gly Ala Arg Pro Asn Arg Ala Ala Thr Ser Gly Tyr
                 85                  90                  95

Trp Lys Ala Thr Gly Thr Asp Lys Pro Val Phe Thr Ser Gly Gly Thr
                100                 105                 110

Gln Lys Val Gly Val Lys Lys Ala Leu Val Phe Tyr Gly Gly Lys Pro
                115                 120                 125

Pro Lys Gly Val Lys Thr Asn Trp Ile Met His Glu Tyr Arg Val Val
            130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
                180                 185                 190

Leu Gly Ser Ile Pro Gln Asn Val Pro Asn Ser Ile Leu Gln Gly Ile
            195                 200                 205

Lys Pro Ser Asn Tyr Gly Thr Ile Leu Leu Glu Asn Glu Ser Asn Met
        210                 215                 220

Tyr Asp Gly Ile Met Asn Asn Thr Asn Asp Ile Ile Asn Asn Asn Asn
225                 230                 235                 240

Arg Ser Ile Pro Gln Ile Ser Ser Lys Arg Thr Met His Gly Gly Leu
                245                 250                 255

Tyr Trp Asn Asn Asp Glu Ala Thr Thr Thr Thr Thr Ile Asp Arg
                260                 265                 270

Asn His Ser Pro Asn Thr Lys Arg Phe Leu Val Glu Asn Glu Asp
            275                 280                 285

Asp Gly Leu Asn Met Asn Asn Ile Ser Arg Ile Thr Asn His Glu Gln
            290                 295                 300

Ser Ser Ser Ile Ala Asn Phe Leu Ser Gln Phe Pro Gln Asn Pro Ser
305                 310                 315                 320

Ile Gln Gln Gln Gln Gln Gln Glu Glu Val Leu Gly Ser Leu Asn
                325                 330                 335

Asp Gly Val Val Phe Arg Gln Pro Tyr Asn Gln Val Thr Gly Met Asn
            340                 345                 350

Trp Tyr Ser
        355

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
tgaattcagg tcaactcaaa catcgtaaat tg                                      32

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
```

-continued

```
      Oligonucleotide

<400> SEQUENCE: 4
aattcacttt ttacacgtta tcgtggatat cttttg                              36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
aaagtagtgg acaaacataa agtagtggac ccataa                              36

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
tgaaagttga atcaagtcat ctacaacaac aaca                                34

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
aatgaaaatc ctgaatcggc cactaactttt aac                                33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
atgattgatt gatcgattga ttttacaggg cta                                 33
```